United States Patent [19]
Mitsuoka et al.

[11] Patent Number: 5,296,221
[45] Date of Patent: Mar. 22, 1994

[54] *LACTOBACILLUS JOHNSONII* FERM BP-2680 LACTIC ACID BACTERIA PREPARATIONS USING THE SAME AND A PROCESS OF MANUFACTURING THE PREPARATIONS

[75] Inventors: Tomotari Mitsuoka, Ichikawa; Kazumasa Suzuki, Ayase; Mitsugu Hayashi, Hisai; Umeyuki Doi; Tsuneo Hadeishi, both of Chita, all of Japan

[73] Assignee: Sani-Ei Sucrochemical Co., Ltd., Chita, Japan

[21] Appl. No.: 51,274

[22] Filed: Apr. 23, 1993

Related U.S. Application Data

[63] Continuation of Ser. No. 768,442, Nov. 27, 1991, abandoned.

[30] Foreign Application Priority Data

Jan. 31, 1990 [JP] Japan .................. 2-19100

[51] Int. Cl.$^5$ .......... A61K 37/00; C12N 1/00; C12N 1/20
[52] U.S. Cl. .................. 424/93 J; 435/243; 435/252.1; 435/252.9; 435/853
[58] Field of Search ........... 435/243, 252.1, 252.9, 435/853; 424/93 J

[56] References Cited

U.S. PATENT DOCUMENTS

| | | | |
|---|---|---|---|
| 1,540,951 | 6/1925 | Reichel et al. .................. | 435/854 |
| 4,579,734 | 4/1986 | Hata et al. .................. | 435/252.9 |
| 4,946,791 | 8/1990 | Manfredi et al. .................. | 435/252.9 |
| 4,954,450 | 9/1990 | Brotherson et al. .................. | 435/252.9 |
| 4,980,164 | 12/1990 | Manfredi et al. .................. | 435/252.9 |

FOREIGN PATENT DOCUMENTS 0896071  1/1982  U.S.S.R. .................. 435/854

*Primary Examiner*—Douglas W. Robinson
*Assistant Examiner*—Deborah K. Ware
*Attorney, Agent, or Firm*—Beveridge, DeGrandi, Weilacher & Young

[57]  ABSTRACT

The present invention comprises a novel strain of *Lactobacillus johnsonni* FERM BP-2680, a lactic acid bacteria preparation using the *Lactobacillus johnsonni* FERM BP-2680, and a process of manufacturing the lactic acid bacteria preparation. The process includes the steps of inoculating the *Lactobacillus johnsonni* FERM BP-2680 into a medium containing fermentable sugar as a major carbon source, cultivating and proliferating under cultivation conditions adapted to anaerobes or facultative anaerobes, and further isolating the *Lactobacillus johnsonni* from the medium and drying the isolated *Lactobacillus johnsonni* with a protective agent to produce the lactic acid bacteria preparation. Optionally a bulking agent may be added to control cell concentration of the preparation. The preparation containing *Lactobacillus johnsonni* FERM BP-2680 is used to suppress harmful bacteria in the digestive tract of mammals.

6 Claims, No Drawings

LACTOBACILLUS JOHNSONII FERM BP-2680 LACTIC ACID BACTERIA PREPARATIONS USING THE SAME AND A PROCESS OF MANUFACTURING THE PREPARATIONS

This application is a continuation of application Ser. No. 07/768,442, filed Nov. 27, 1991, now abandoned, which application is entirely incorporated herein by reference.

TECHNICAL FIELD

The present invention relates to *Lactobacillus johnsonni* F-133, lactic acid bacteria preparations using the same, and a process of manufacturing the preparations.

BACKGROUND ART

It has been well known that lactic acid bacteria are distributed as normal bacterial floras (enteric bacilli) in intestinal tracts and cavities of human beings or animals and are useful for maintaining their health. Recently, remarkable progress in study of intestinal micro-floras (hereinafter may be referred to as "floras") has gradually revealed a role of lactic acid bacteria.

In this connection, attention is drawn to the effects of lactic acid bacteria preparations and various kinds of food including lactic acid bacteria, such as fermented milk and sour milk beverage.

Generally speaking, such intestinal floras comprise a group of lactic acid bacteria, an anaerobic group, and an aerobic group.

These intestinal floras comprise useful bacteria, such as lactic acid bacteria, which are useful to human beings and animals, and harmful bacteria which are harmful to the contrary. Such useful and harmful bacteria both live in intestines with a specific balance kept therebetween.

Herein, the term "useful bacteria" indicates those bacteria which are useful to maintain the health of a host by various activities, for example, synthesis of vitamin and protein, promotion of digestion and absorption, suppression of proliferation of foreign bacteria, stimulation of immune functions, or the like. On the other hand, the term "harmful bacteria" indicates those bacteria which produce in intenstines various materials that are harmful to the host and are therefore considered to relate to the causes of various acute or chronic diseases, senility, and cancer.

Accordingly, it is understood that human diseases, senility, and cancer can be avoided and human being can stay being healthy, if harmful bacteria in intestines are suppressed and useful bacteria are increased to the contrary.

As regards livestock, it has been well known that administration of useful bacteria, such as lactic acid bacteria, or fermented products thereof is effective in promoting growth and in preventing and curing diseases such as diarrhea. Recently, such application has been widely made.

These preparations are called probiotics and has become into worldwide use.

In the meanwhile, infant animals are inherently germ-free when they are born. As soon as they are born, various bacteria begin enter into their bodies environment.

The balance between useful bacteria and harmful bacteria in intestinal floras of infant animals gradually become stable with the lapse of days after birth. However, the balance is often affected by environment and change of feed.

Specifically, in infant animals, useful bacteria are liable to decrease while opportunistic *Escherichia coli* is liable to profiferate rapidly.

Proliferation of opportunistic *Escherichia coli* breaks the balance in intestinal floras to often cause diseases.

If viable cell preparations such as lactic acid bacteria preparations are preventively administered to infant animals, the acidity of their intestines can be maintained. In this event, proliferation of *Escherichia coli* is suppressed so as to effectively prevent various diseases resulting from imbalance in intestinal floras.

Administration of such viable cell preparations generally has a remarkable effect on infant animals. If applied to healthy adult animals, a considerable effect is also observed.

Intestinal floras of adult animals maintain a delicate balance which is not always constant. The balance is easily broken due to stimulation by environment, such as stress.

Specifically, the balance in intestinal floras is highly dependent on a pH in intestines.

If lactic acid bacteria are predominant and produce lactic acid sufficiently, the acidity in intestines is maintained so as to suppress proliferation of *Escherichia coli*.

On the contrary, when the activity of lactic acid bacteria is diminished, organic acid such as lactic acid is reduced. In this event, *Escherichia coli* readily proliferates to thereby cause diseases such as diarrhea.

For viable cell preparations, use may be made of intestinal bacteria derivatives or other bacteria that are not belong to normal intestinal bacteria. Intestinal bacteria derivatives which can proliferate in intestines of animals dosed are desirable.

However, some intestinal bacteria cannot colonize in intestines of animals of different species because of specific characteristics.

In other words, even if particular intestinal bacteria are inherent to a particular animal, they are liable to be eliminated by indigenous bacteria in case when they are administered from outside. It is to be noted that colonization and proliferation in intestines would not always be expected.

Accordingly, if further administration of bacteria is stopped, the bacteria that have already been supplied disappear from intestines in a relatively short period of time.

It is reported that, even in such case, continuous administration of more than a predetermined amount of viable cell preparations is effective in preventing and curing diarrhea and in promoting growth, irrespective of colonization. This is because the administered bacteria themselves act in intestines or aid to maintain and proliferate useful bacteria that have indigenously existed in intestines.

Generally, in order to improve efficiency of viable cell preparations, a necessary amount of viable cells must reach intestines through a stomach.

Therefore, essential properties required to the bacteria are: to be stable in preparations; to be stable in feed or drinking water into which the preparations are mixed; to be acid-resistant in a stomach that shows high acidity among other digestive tracts; and to be resistant to sterilizing action of bile in small intestines.

In addition, recent and strong demand exists for viable cell preparations in that viable cells have high activity to perform intestinal action with high efficiency.

Desirably, viable cells sufficiently proliferate so as to colonize in intestines. It is at least necessary for viable cells to be highly effective in promoting proliferation of indigenous lactic acid bacteria.

Such viable cell preparations must have a high survival stability of bacteria in the preparations. In addition, the viable cell preparations must reach inside of intestines against severe conditions in digestive tracts.

Even though many viable cell preparations are commercially available at present, no preparations sufficiently meets these requirements.

It is an object of the present invention to find a lactic acid bacteria strain satisfying the requirements for viable cell preparations and to provide lactic acid bacteria preparations having a sufficient survival stability and satisfying various requirements, and a manufacturing process of the preparations.

DISCLOSURE OF THE INVENTION

The present inventors have sought lactic acid bacteria satisfying the above-mentioned requirements. The inventors isolated various lactic acid bacteria strains from intestines of various animals such as cows, pigs, and chickens, and cultivated those strains to investigate characteristics of bacteria. As a result, the present inventors succeeded to obtain an excellent lactic acid bacteria strain which meets the object of the present invention by means of pure isolation from intestines of cows in a known manner.

The present invention comprises a novel strain of Lactobacillus johnsonii F-133 (FRI International Deposit No. 2680), lactic acid bacteria preparations using the Lactobacillus johnsonii F-133 (FRI International Deposit No. 2680), and a process of manufacturing the lactic acid bacteria preparations comprising the steps of: inoculating the Lactobacillus johnsonii F-133 (FRI International Deposit No. 2680) into a medium comprising fermentable sugar as a major carbon source; cultivating and proliferating under cultivation conditions adapted to facultative anaerobes; and then isolating bacteria into lactic acid bacteria preparations.

The Lactobacillus johnsonii F-133 according to the present invention was deposited in Fermentation Research Institute (in Ibaraki, Japan) of Agency of Industrial Science and Technology belonging to Ministry of International Trade and Industry, on Oct. 20, 1989 as FRI Microorganism Deposit No. P-11064 (FERM P-11064). Thereafter, it was transferred to International Depository in the same institute on Dec. 13, 1989 and the deposit number was changed to FRI International Deposit No. 2680 (FERM BP-2680).

The novel Lactobacillus johnsonii F-133 has the following mycological characteristics.

(a) To be gram-positive, non-sporeforming, facultative anaerobic rods.

(b) To ferment glucose and produce lactic acid (DL). No gas is produced from glucose. Growing at 15° C. and non-motile. The acid is produced from glucose, mannose, fructose, galactose, sucrose, maltose, cellobiose, lactose, trehalose, dextrin, starch, esculin, salicin, and amygdalin. To the contrary, no acid is produced from arabinose, xylose, rhamnose, ribose, melibiose, raffinose, melezitose, sorbitol, and mannitol. Excellent growth in BL agar medium, LBS agar medium, MRS agar medium, and Briggs Liver Broth.

(c) The bacteria of the invention are identified as Lactobacillus acidophilus in phenotype (the above-mentioned properties). However, in DNA homology, the bacteria are not defined to be Lactobacillus acidophilus but to be those that are similar to Lactobacillus acidophilus and belong to the Lactobacillus acidophilus group.

In view of the above-mentioned mycological properties, the bacteria are judged to be a novel microorganism belonging to the Lactobacillus acidophilus group and are named Lactobacillus johnsonii F-133.

Description will now be made as regards a process of manufacturing lactic acid bacteria preparations using the above-mentioned Lactobacillus johnsonii F-133.

The lactic acid bacteria preparations are manufactured by (a) inoculating the Lactobacillus johnsonii F-133 into a medium containing: fermentable sugar such as glucose, fructose, and sucrose as a major carbon source; nitrogen compound which may be used by microorganisms such as peptone, malt extract, corn steep liquor, and yeast extract as a nitrogen source; inorganic salt such as ferrous sulfate, manganese sulfate, sodium acetate, and potassium monohydrogenphosphate; and Tween 80, (b) cultivating and proliferating under cultivation conditions adapted to facultative anaerobes, (c) washing and isolating bacteria, (d) drying with a protective agent, and (e) adding a bulking agent to control the cell concentration depending upon the use.

Preferably, Lactobacillus johnsonii F-133 is cultivated by the use of a liquid medium under anaerobic conditions. However, completely anaerobic conditions are unnecessary because the bacteria are facultative anaerobic.

As a major carbon source of the liquid medium, use is made of sugar such as glucose, fructose, and sucrose. The sugar is contained in the medium at a rate of 1–20% (W/V). A range of 4–8% (W/V) is especially preferable.

Cultivation is carried out at a temperature in the range which allows the growth of microorganisms, namely, between 20° C. and 45° C. A temperature between 30° C. and 40° C. is especially preferable.

Cultivation is carried out with the pH adjusted in the range between 3 and 8, preferably between 5 and 7.

The cultivation time differs dependent on kinds of culture media used and the concentration of sugar as a major carbon source. Generally, it takes 10–24 hours.

As regards the cultivation time, it is desirable to finish the cultivation according to the present invention at a time when the cell count of microorganisms becomes maximum. If cultivation is continued further, the microorganisms begin to reduce and the preparations manufactured have a less survival rate of microorganisms.

Cultivation may be carried out also by inoculating into a liquid medium a seed culture solution preliminarily cultured, instead of direct inoculation of Lactobacillus johnsonii F-133.

The microorganisms in a culture solution thus obtained are isolated in a known manner.

Specifically, the microorganisms are isolated by a known method normally used in such case in this field of art, for example, by means of membrane filtration or centrifugal separation.

For example, a culture solution containing the microorganisms obtained is filtered by the use of an organic membrane. After 10-fold condensation of the concentration of the microorganisms, washing liquid is added to the amount equal to that of the condensed microorganism solution. Filtration and washing are carried out by the use of an organic membrane until the volume becomes equal to ⅓. The operation is repeated three times.

Herein, the washing liquid is prepared from corn steep liquor (concentration of 7° Bx) by adding 2% glucose (W/V). After diluted to the concentration of 3° Bx, the liquid is neutralized by sodium hydroxide and resultant deposition is removed.

A protective agent is added to the condensed microorganism solution after washing. The pH is adjusted by sodium hydroxide and the like. By the use of a freeze dryer, the solution is dried until the water content becomes equal to 4% or less. Thus, lactic acid bacteria preparations are obtained.

Dependent on use, a bulking agent consisting of any one of skim milk, lactose, starch, and the like, or a combination thereof may be added to control the density of microorganisms so as to manufacture a desired type of lactic acid bacteria preparations.

The lactic acid bacteria preparations may be formed into granules, pellets, and tablets instead of powders.

Ingredients of the above-mentioned protective agent and the amounts added relative to the washed condensed microorganism solution are exemplified below.

Skim milk: 10% (W/V)
Sodium glutamate: 1% (W/V)
L-ascorbic acid: 0.5% (W/V)
L-cysteine: 0.05% (W/V)

BEST MODE FOR EMBODYING THE INVENTION

Embodiments

Embodiments of the present invention will be described below.

EXAMPLE 1

Corn steep liquor (concentration of 5° Bx) to which 6% (W/V) glucose and 0.2% (W/V) Tween 80 are added is filtered by a 0.1 μm sterilizing membrane filter (PSV303 manufactured by Asahi Chemical Industry Co., Ltd.) to be used as a medium.

200 liter of the above-mentioned medium is introduced into a 300 liter tank fermenter (manufactured by Komatsugawa Chemical Engineering Co., Ltd.) through a sterilizing membrane filter provided with an organic membrane (PSV303 manufactured by Asahi Chemical Industry Co., Ltd.) having a pore size of 0.1 μm. The pH is adjusted to 5.5 by 12N sodium hydroxide.

Next, the temperature is adjusted to 37° C. Inoculum ($10^9$/ml) of the *Lactobacillus johnsonii* F-133 strain is preliminarily cultivated in a medium similar to the above-mentioned medium for 16 hours. 2 liter of the inoculum is inoculated into the medium. Agitating cultivation is carried out at a temperature of 37° C. while the inoculum is maintained to have the pH of 5.5 for 16 hours.

In this event, the pH is adjusted by adding 12N sodium hydroxide through an automatic controller.

The cell count in the culture solution is equal to $3 \times 10^9$/ml at the end of cultivation.

The culture solution is filtered by a fine filter provided with an organic membrane (PSV313 manufactured by Asahi Chemical Industry Co., Ltd.) having a pore size of 0.1 μm and condensed to 20 liter.

Subsequently, 20 liter of washing liquid that is preliminarily prepared is added to the condensed solution. Similar filtration is carried out until the volume is condensed to 20 liter.

The operation is repeated three times.

The washing liquid is prepared by neutralizing 25 liter corn steep liquor having the concentration of 7° Bx with 12N sodium hydroxide, precipitating the deposition, taking 20 liter of the supernatant, adding 2% glucose thereto, and diluting into 60 liter.

2 kg of skim milk, 200 g of sodium glutamate, 100 g of L-ascorbic acid, and 10 g of L-cysteine are added and dissolved into 20 liter of condensed bacteria solution after washing. The pH is adjusted to 7 by 4N sodium hydroxide.

The bacteria solution is freezed at −40° C. By using an RLE-308 freeze dryer (manufactured by Kyowa Vacuum Engineering Co., Ltd.), the solution is subjected to preliminary drying at 50° C. for 60 minutes, primary drying at 70° C. for 150 minutes, and secondary drying at 30° C. for 14 hours. After drying water content is equal to 3.5% while the number of viable cells is equal to $5 \times 10^{10}$/g.

EXAMPLE 2

Corn steep liquor (concentration of 7° Bx) to which 2% (W/V) glucose and 0.2% (W/V) Tween 80 are added is introduced into a medium supply tank of a lactic acid bacteria continuous fermenter (manufactured by Kansai Chemical Machinery Manufacturing Co., Ltd.) through a 0.1 μm sterilizing membrane filter (PSV303 manufactured by Asahi Kasei Kogyo Co. Ltd.).

The medium supplied to the medium supply tank is delivered to a reactor section at 14 liter/h to circulate a reactor system.

5 liter of inoculum of the *Lactobacillus johnsonii* F-133 strain that is preliminarily cultivated is injected for inoculation into the reactor circulation system. The pH is adjusted to 5.5 by 12N sodium hydroxide. The temperature is maintained at 37° C. Then, cultivation is started.

The reactor system is provided with an organic membrane (PSV313 manufactured by Asahi Kasei Kogyo Co., Ltd.) having a pore size of 0.1 μm. A new medium is supplied in synchronism with successive filtration of the fermentation medium.

The cell concentration in the culture solution is measured at OD 660 nm. When OD 660 nm of 100-fold dilution reaches 1.0, the bacteria solution is extracted at a rate of 750 ml/h.

The number of viable cells at this moment is equal to $2 \times 10^{10}$/ml.

The bacteria solution pumped out is washed and dried in the manner similar to Example 1.

After drying, the water content is equal to 3.7% while the number of viable cells is equal to $3 \times 10^{10}$/g.

EXAMPLE 3

Cultivation is carried out in the manner similar to Example 2. Washing of bacteria is carried out by the use of a high speed cetrifuge.

Specifically, the bacteria solution that has been continuously pumped out from the lactic acid bacteria continuous fermenter is centrifuged at 6000 rpm for 10 minutes. The supernatant is deleted. The bacteria precipitation is suspended in the washing liquid shown in Example 1 to recover the volume before centrifugal operation. Centrifugal operation is repeated again.

After such washing is repeated again, drying is carried out like Example 1.

After drying, the water content is equal to 3.1% while the number of viable cells is equal to $4 \times 10^{10}/g$.

Test

Next, description will be made as regards a stomach acid resistance test (Test 1), a bile acid resistance test (Test 2), and a growth suppression test for pathogenic bacteria (Test 3) in connection with *Lactobacillus johnsonii* F-133 of the present invention.

In those tests, *Lactobacillus johnsonii* F-133 (FRI International Deposit No. 2680) is used as the strain of the invention. The following strains are used as comparative strains 1-6. Each test is carried on seven kinds of lactic acid bacteria strains in total.

Comparative Strain 1 (cow derivative)
  Lactobacillus amylovorus F-81
Comparative Strain 2 (pig derivative)
  Lactobacillus amylovorus F-100
Comparative Strain 3 (pig derivative)
  Lactobacillus amylovorus I-80
Comparative Strain 4 (chicken derivative)
  Lactobacillus crispapus F-3
Comparative Strain 5 (commercially available)
  Bacillus coagulans
Comparative Strain 6 (commercially available)
  Lactobacillus acidophilus M-13

Test 1

The stomach acid resistance test is carried out in the following manner. Each sample strain is individually added to each of pH1, pH2, and pH3 hydrochloric acid solutions to be subjected to the action of the acid in a constant temperature bath kept at 37° C. The number of surviving cells of lactic acid bacteria in each hydrochloric acid solution is counted after 0 hour (immediately after addition), 0.5 hour, 1 hour, 3 hours, and 5 hours, respectively.

Table 1 shows the change of number of viable cells of each sample strain in 1 ml of pH1, pH2, and pH3 hydrochloric acid solutions with the lapse of time.

Test 1 is carried out under the following conditions.
(a) Pre-culture medium
  MRS agar medium (OXOID)
(b) Cell count Medium
  MRS agar medium (OXOID)
(c) Preparation of bacteria solution After anaerobic culture of each strain in the preculture medium at 35° C. for 2 days, the bacteria are suspended in a sterilized physiological saline solution to form a bacteria solution.

(d) Test solution

Each of pH1, pH2, and pH3 hydrochloric acid solutions is sterilized by an autoclave at 121° C. for 15 minutes and then cooled for test.

(e) Action

The bacteria solution is added to the test solution at a rate of 1 ml: 100 ml so that the number of viable cells per 1 ml is equal to $10^5 - 10^6$. Action is carried out in a constant temperature bath kept at 37° C. for 0 hour (immediately after the addition), 0.5 hour, 1 hour, 3 hours, and 5 hours, respectively.

(f) Culture

The number of surviving cells of sample strains in the test solution after being subjected to the action of the acid is counted by the use of a layer plate method (aerobic culture at 35° C. for two days) using the cell count medium.

TABLE 1

| pH | sample strains | 0 (immediately after the addition) | 0.5 | 1 | 3 | 5 |
|---|---|---|---|---|---|---|
| pH 1 | strain of the invention | $1.8 \times 0^6$ | 40 | 10 or less | 10 or less | 10 or less |
| | comparative strain 1 | $5.1 \times 10^5$ | 10 or less | 10 or less | 10 or less | 10 or less |
| | comparative strain 2 | $2.7 \times 10^6$ | 10 or less | 10 or less | 10 or less | 10 or less |
| | comparative strain 3 | $1.3 \times 10^6$ | 10 or less | 10 or less | 10 or less | 10 or less |
| | comparative strain 4 | $7.2 \times 10^5$ | 10 or less | 10 or less | 10 or less | 10 or less |
| | comparative strain 5 | $9.4 \times 10^6$ | 10 or less | 10 or less | 10 or less | 10 or less |
| | comparative strain 6 | $1.9 \times 10^6$ | 10 or less | 10 or less | 10 or less | 10 or less |
| pH 2 | strain of the invention | $2.0 \times 10^6$ | $1.6 \times 10^6$ | $1.3 \times 10^6$ | $8.8 \times 10^5$ | $3.2 \times 10^5$ |
| | comparative strain 1 | $2.8 \times 10^6$ | $2.4 \times 10^5$ | $2.5 \times 10^2$ | 10 or less | 10 or less |
| | comparative strain 2 | $4.8 \times 10^6$ | $5.6 \times 10^3$ | 10 or less | 10 or less | 10 or less |
| | comparative strain 3 | $1.5 \times 10^6$ | $1.3 \times 10^4$ | $1.9 \times 10^2$ | 10 or less | 10 or less |
| | comparative strain 4 | $7.2 \times 10^5$ | $4.0 \times 10^3$ | 10 or less | 10 or less | 10 or less |
| | comparative strain 5 | $8.6 \times 10^5$ | $3.4 \times 10^3$ | 10 | 10 or less | 10 or less |
| | comparative strain 6 | $1.4 \times 10^6$ | $2.1 \times 10^2$ | 10 or less | 10 or less | 10 or less |
| pH 3 | strain of the invention | $1.4 \times 10^6$ | $1.0 \times 10^6$ | $4.4 \times 10^5$ | $1.7 \times 10^5$ | $4.8 \times 10^4$ |
| | comparative strain 1 | $6.4 \times 10^5$ | $2.0 \times 10^5$ | $1.2 \times 10^3$ | 60 | 10 or less |
| | comparative strain 2 | $5.0 \times 10^5$ | $3.0 \times 10^2$ | 10 | 10 or less | 10 or less |
| | comparative strain 3 | $2.4 \times 10^5$ | $5.0 \times 10^4$ | $9.9 \times 10^3$ | 70 | 10 or less |
| | comparative strain 4 | $1.0 \times 10^5$ | $3.2 \times 10^3$ | 20 | 10 or less | 10 or less |
| | comparative strain 5 | $1.2 \times 10^4$ | 10 or less | 10 or less | 10 or less | 10 or less |
| | comparative strain 6 | $3.2 \times 10^5$ | $1.6 \times 10^5$ | $5.3 \times 10^4$ | $6.0 \times 10^2$ | $3.0 \times 10^2$ |

Test 2

The bile acid resistance test is carried out by measuring a minimum inhibitory concentration of bile powder for plate media having the pH of 5, 6, and 7.

Specifically, the bile powder is added to each plate medium (MRS agar medium) to various concentration levels. The sample strain (lactic acid bacteria) is smeared to the medium and cultivated. The minimum concentration of bile powder of cows when the growth is inhibited is regarded to be a minimum inhibitory concentration of bile powder against sample bacteria. The results are shown in Table 2.

Test 2 is carried out under the following conditions.
(a) Enrichment culture medium
  MRS bouillon (OXOID)
(b) Sensitivity measuring medium
  MRS agar medium (OXOID)
(c) Bile powder
  Bile powder of cows [manufactured by Wako Pure Chemical Industries, Ltd.]

(d) Preparation of plate medium for measuring sensitivity

A 20000 ppm suspension of bile powder is prepared by the use of sterilized purified water and is diluted in 2-fold. Thus, 10000, 5000, 2500, 1250, 625, 313, 156, 78, and 39 ppm suspensions are prepared.

Next, the sensitivity measuring medium heated and melted is supplied with each of the above-mentioned suspensions having various dilution levels in the amount equal to 1/9 of the medium. Then, the pH is adjusted to pH5, pH6, and pH7. After sufficiently mixing, the mixture is distributed each into different petri dishes to be solidified. Thus, the sensitivity measuring plate medium is formed.

As described above, three kinds of the sensitivity measuring plate series having pH5, pH6, and pH7 are prepared.

(e) Preparation of inoculum bacteria solution Sample strains subcultured in the enrichment medium are inoculated, cultivated, and diluted by the same medium so that the cell count become equal to $10^6$/ml.

(f) Cultivation

Inoculum bacteria solution is smeared into the sensitivity measuring plate medium (each series of pH5, pH6, and pH7) by a streak of the order of 2 cm or so drawn by Nichrome wire (having inner diameter of about 1 mm). Anaerobic culture is carried out at 35° C. for 18-20 hours.

(g) Judgement

After cultivating for a predetermined period of time, the minimum concentration at which the growth is inhibited is regarded as a minimum inhibitory concentration of bile powder against the sample strains.

Test 3 is carried out under the following conditions.

(a) Tested pathogenic bacteria

*Escherichia coli* IFO 3301 (*Escherichia coli*)

*Salmonella typhimurium* Laboratory strain (Salmonella)

*Pseudomonas aeruginosa* IID P-1 (*Pseudomonas aeruginosa*)

(b) Preculture medium

Tested pathogenic bacteria: ordinary agar slant medium Sample strain (lactic acid bacteria): MRS medium (c) Preparation of inoculum bacteria solution As regards the tested pathogenic bacteria, the preculture medium after cultivated at 35° C. for one night is suspended in the MRS medium so that the number of viable cells is equal to $10^3 - 10^5$ per 1 ml. Thus, bacteria solution is prepared.

As regards the lactic acid bacteria, preculture medium after cultivated at 35° C. for one night is diluted by the same medium so that the number of viable cells is equal to $10^3 - 10^5$ per 1 ml.

(d) Test medium

The pH of the MRS medium is adjusted at 7.0 by adding sodium hydroxide solution.

(e) Cell count medium

*Escherichia coli, Salmonella typhimurium*: DHL agar medium

*Pseudomonas aeruginosa*: ½ cetrimide medium

Lactic acid bacteria: MRS agar medium added with 1 ppm colistin sulphate (f) Culture Inoculum bacteria solution is added to the test medium at a rate of 1 ml/100 ml so that the cell count is equal to $10 - 10^3$ per 1 ml of the test medium for each

TABLE 2

| sample strains | pH of plate medium | | |
|---|---|---|---|
| | pH 5 | pH 6 | pH 7 |
| strain of the invention | 2,000 ppm or more | 2,000 ppm or more | 2,000 ppm or more |
| comparative strain 1 | 2,000 ppm or more | 2,000 ppm or more | 2,000 ppm or more |
| comparative strain 2 | 2,000 ppm or more | 2,000 ppm or more | 2,000 ppm |
| comparative strain 3 | 2,000 ppm or more | 2,000 ppm or more | 2,000 ppm or more |
| comparative strain 4 | 2,000 ppm or more | 2,000 ppm or more | 2,000 ppm or more |
| comparative strain 5 | 125 ppm | 2,000 ppm or more | 2,000 ppm |
| comparative strain 6 | 2,000 ppm or more | 2,000 ppm or more | 2,000 ppm or more |

Test 3

The growth suppression test against pathogenic bacteria is carried out by selecting *Escherichia Coli, Salmonella typhimurium*, and *Pseudomonas aeruginosa*, as intestinal pathogenic bacteria, and by measuring growth suppression effects of each sample strain (lactic acid bacteria) against these pathogenic bacteria.

Specifically, strains of the pathogenic bacteria (*Escherichia Coli, Salmonella typhimuruim*, and *Pseudomonas aeruginosa*) and the sample strains (lactic acid bacteria) are individually or in combination added to liquid media and subjected to shaking culture. After 0 hour (theoretical number of added bacteria), 3 hours, 6 hours, 9 hours, and 24 hours, the number of viable cells in 1 ml of each liquid medium and pH of each liquid medium are measured.

Table 3-1 and Tables 3-2 through 3-7 show the results for the strain of the present invention and the comparative strains 1-6, respectively.

strain. After sufficiently mixing, shaking culture is carried out in a constant temperature bath kept at 37° C. for 0 hour (theoretical number of added bacteria), 3 hours, 6 hours, 9 hours, and 24 hours, respectively.

The test is carried out as regards the cases when the tested pathogenic bacteria and the sample strains (lactic acid bacteria) are inoculated in combination into the same test medium and the cases when the tested pathogenic bacteria and the sample strains are individually inoculated into the different test media.

(g) Viable cell count

The number of viable cells in the test medium cultivated as described above is counted by the use of the cell count medium.

In order to count the number of lactic acid bacteria, cultivation is carried out in a layer plate method (at 35° C. for 2 days). On the other hand, in order to count the number of the tested pathogenic bacteria (*Escherichia coli, Salmonella typhimurium*, and *Pseudomonas aeruginosa*), cultivation is carried out in a pour-plate method (at 35° C. for 2 days).

TABLE 3-1

| added bacteria | measured strains | 0 (theoretical number of added bacteria) | shaking time (hr) 3 | 6 | 9 | 24 |
|---|---|---|---|---|---|---|
| strain of the invention | strain of the invention | 7.5 (6.5) | $2.6 \times 10^2$ (6.4) | $6.8 \times 10^3$ (5.9) | $4.5 \times 10^4$ (6.4) | $4.8 \times 10^6$ (3.9) |
| Escherichia Coli | Escherichia Coli | $1.5 \times 10^2$ (6.5) | $2.5 \times 10^2$ (6.4) | $1.5 \times 10^4$ (6.3) | $2.2 \times 10^4$ (6.4) | $2.3 \times 10^6$ (4.6) |
| Escherichia Coli + strain of the invention | Escherichia Coli | $1.5 \times 10^2$ (6.5) | $3.1 \times 10^2$ (6.5) | $2.0 \times 10^4$ (6.3) | $2.1 \times 10^5$ (6.4) | 0 (3.1) |
| strain of the invention | strain of the invention | 75 (6.5) | $3.3 \times 10^2$ (6.5) | $8.1 \times 10^3$ (6.3) | $2.4 \times 10^4$ (6.4) | $1.8 \times 10^9$ (3.1) |
| Salmonella typhimurium | Salmonella typhimurium | $1.5 \times 10^2$ (6.5) | $3.4 \times 10^2$ (6.5) | $2.3 \times 10^4$ (6.2) | $3.9 \times 10^5$ (6.2) | $3.1 \times 10^8$ (4.5) |
| Salmonella typhimurium + strain of the invention | Salmonella typhimurium | $1.5 \times 10^2$ (6.5) | $3.2 \times 10^2$ (6.5) | $1.4 \times 10^4$ (6.3) | $2.9 \times 10^5$ (6.4) | 0 (3.1) |
| strain of the invention | strain of the invention | 75 (6.5) | $3.8 \times 10^2$ (6.6) | $7.6 \times 10^3$ (6.0) | $3.2 \times 10^4$ (6.2) | $8.6 \times 10^8$ (3.1) |
| Pseudomonas aeruginosa | Pseudomonas aeruginosa | 72 (6.5) | $1.8 \times 10^2$ (6.9) | $1.6 \times 10^2$ (6.3) | $4.8 \times 10^2$ (6.4) | $6.4 \times 10^6$ (6.4) |
| Pseudomonas aeruginosa + strain of the invention | Pseudomonas aeruginosa | 72 (6.5) | $1.6 \times 10^2$ (6.5) | $2.5 \times 10^2$ (6.4) | $6.4 \times 10^2$ (6.3) | 0 (3.3) |
| strain of the invention | strain of the invention | 75 (6.5) | $4.0 \times 10^2$ (6.5) | $7.9 \times 10^3$ (6.3) | $5.6 \times 10^4$ (6.3) | $1.1 \times 10^8$ (3.3) |

Figure in parenthesis shows pH of medium.

TABLE 3-2

| added bacteria | measured strains | 0 (theoretical number of added bacteria) | shaking time (hr) 3 | 6 | 9 | 24 |
|---|---|---|---|---|---|---|
| comparative strain 1 | comparative strain 1 | $6.8 \times 10^2$ (6.7) | $1.6 \times 10^3$ (6.7) | $1.7 \times 10^4$ (6.7) | $7.2 \times 10^4$ (6.5) | $6.9 \times 10^7$ (5.2) |
| Escherichia Coli | Escherichia Coli | 58 (6.7) | 87 (6.7) | $1.3 \times 10^4$ (6.7) | $2.0 \times 10^5$ (6.6) | $2.0 \times 10^6$ (5.5) |
| Escherichia Coli + comparative strain 1 | Escherichia Coli | 58 (6.7) | 95 (6.6) | $4.2 \times 10^3$ (6.7) | $1.3 \times 10^5$ (6.7) | $9.2 \times 10^4$ (4.7) |
| comparative strain 1 | comparative strain 1 | $6.8 \times 10^2$ (6.7) | $1.3 \times 10^3$ (6.6) | $8.0 \times 10^4$ (6.7) | $4.6 \times 10^4$ (6.7) | $4.3 \times 10^8$ (4.7) |
| Salmonella typhimurium | Salmonella typhimurium | $5.1 \times 10^2$ (6.7) | $1.1 \times 10^3$ (6.7) | $6.7 \times 10^4$ (6.7) | $1.8 \times 10^6$ (6.7) | $4.1 \times 10^9$ (5.4) |
| Salmonella typhimurium + comparative strain 1 | Salmonella typhimurium | $5.1 \times 10^2$ (6.7) | $1.1 \times 10^3$ (6.6) | $3.3 \times 10^4$ (6.7) | $8.8 \times 10^5$ (6.7) | $4.5 \times 10^7$ (4.7) |
| comparative strain 1 | comparative strain 1 | $6.8 \times 10^2$ (6.7) | $1.3 \times 10^3$ (6.7) | $1.4 \times 10^4$ (6.6) | $4.3 \times 10^4$ (6.7) | $1.0 \times 10^9$ (4.7) |
| Pseudomonas aeruginosa | Pseudomonas aeruginosa | $1.2 \times 10^2$ (6.7) | $1.8 \times 10^2$ (6.7) | $2.4 \times 10^2$ (6.7) | $3.0 \times 10^2$ (6.6) | $1.2 \times 10^8$ (7.0) |
| Pseudomonas aeruginosa + comparative strain 1 | Pseudomonas aeruginosa | $1.2 \times 10^2$ (6.7) | 72 (6.7) | $1.2 \times 10^2$ (6.7) | $2.1 \times 10^2$ (6.7) | $1.5 \times 10^4$ (4.9) |
| comparative strain 1 | comparative strain 1 | $6.8 \times 10^2$ (6.7) | $1.4 \times 10^3$ (6.7) | $1.1 \times 10^4$ (6.7) | $4.5 \times 10^4$ (6.7) | $1.8 \times 10^9$ (4.9) |

Figure in parenthesis shows pH of medium.

TABLE 3-3

| added bacteria | measured strains | 0 (theoretical number of added bacteria) | shaking time (hr) 3 | 6 | 9 | 24 |
|---|---|---|---|---|---|---|
| comparative strain 2 | comparative strain 2 | $1.1 \times 10^2$ (6.8) | $3.7 \times 10^2$ (6.7) | $4.2 \times 10^3$ (6.8) | $3.0 \times 10^4$ (6.7) | $2.8 \times 10^6$ (5.1) |
| Escherichia Coli | Escherichia Coli | 21 (6.8) | 48 (6.8) | $2.1 \times 10^3$ (6.7) | $7.4 \times 10^3$ (6.8) | $1.1 \times 10^9$ (4.4) |
| Escherichia Coli + comparative strain 2 | Escherichia Coli | 21 (6.8) | 49 (6.7) | $1.1 \times 10^3$ (6.7) | $1.5 \times 10^5$ (6.8) | $2.8 \times 10^4$ (4.4) |
| comparative strain 2 | comparative strain 2 | $1.1 \times 10^2$ (6.8) | $3.0 \times 10^2$ (6.8) | $5.6 \times 10^3$ (6.7) | $4.1 \times 10^4$ (6.7) | $1.1 \times 10^9$ (4.4) |
| Salmonella typhimurium | Salmonella typhimurium | $1.8 \times 10^2$ (6.8) | $3.2 \times 10^2$ (6.8) | $5.0 \times 10^2$ (6.7) | $6.7 \times 10^5$ (6.7) | $3.2 \times 10^9$ (5.4) |
| Salmonella typhimurium + comparative strain 2 | Salmonella typhimurium | $1.8 \times 10^2$ (6.8) | $2.3 \times 10^3$ (6.8) | $4.6 \times 10^3$ (6.7) | $3.1 \times 10^5$ (6.7) | $9.8 \times 10^6$ (4.4) |
| comparative strain 2 | comparative strain 2 | $1.1 \times 10^2$ (6.8) | $3.5 \times 10^2$ (6.8) | $7.5 \times 10^3$ (6.7) | $3.4 \times 10^4$ (6.7) | $5.2 \times 10^8$ (4.4) |
| Pseudomonas aeruginosa | Pseudomonas aeruginosa | 22 (6.8) | 19 (6.7) | 23 (6.7) | 28 (6.8) | $1.8 \times 10^6$ (6.8) |
| Pseudomonas aeruginosa + | Pseudomonas aeruginosa | 22 (6.8) | 14 (6.8) | 23 (6.8) | 31 (6.7) | 1 (4.9) |

TABLE 3-3-continued

| | | shaking time (hr) | | | | |
|---|---|---|---|---|---|---|
| added bacteria | measured strains | 0 (theoretical number of added bacteria) | 3 | 6 | 9 | 24 |
| comparative strain 2 | comparative strain 2 | $1.1 \times 10^2$ (6.8) | $4.4 \times 10^2$ (6.8) | $8.6 \times 10^3$ (6.8) | $4.9 \times 10^4$ (6.7) | $1.2 \times 10^6$ (4.9) |

Figure in parenthesis shows pH of medium.

TABLE 3-4

| | | shaking time (hr) | | | | |
|---|---|---|---|---|---|---|
| added bacteria | measured strains | 0 (theoretical number of added bacteria) | 3 | 6 | 9 | 24 |
| comparative strain 3 | comparative strain 3 | 40 (6.8) | $1.6 \times 10^2$ (6.8) | $3.5 \times 10^3$ (6.8) | $4.7 \times 10^4$ (6.8) | $1.0 \times 10^9$ (5.1) |
| Escherichia Coli | Escherichia Coli | 34 (6.8) | 66 (6.8) | $2.2 \times 10^3$ (6.7) | $1.0 \times 10^3$ (6.8) | $6.4 \times 10^8$ (5.7) |
| Escherichia Coli + | Escherichia Coli | 34 (6.8) | 52 (6.8) | $1.9 \times 10^3$ (6.8) | $7.0 \times 10^3$ (6.8) | $9.6 \times 10^6$ (4.8) |
| comparative strain 3 | comparative strain 3 | 40 (6.8) | $1.6 \times 10^2$ (6.8) | $3.0 \times 10^3$ (6.8) | $5.0 \times 10^4$ (6.8) | $1.2 \times 10^{10}$ (4.8) |
| Salmonella typhimurium | Salmonella typhimurium | $1.8 \times 10^2$ (6.8) | $1.6 \times 10^2$ (6.8) | $1.3 \times 10^3$ (6.8) | $6.0 \times 10^5$ (6.8) | $2.4 \times 10^9$ (5.6) |
| Salmonella typhimurium + | Salmonella typhimurium | $1.8 \times 10^2$ (6.8) | $1.2 \times 10^2$ (6.8) | $1.5 \times 10^3$ (6.8) | $2.8 \times 10^5$ (6.8) | 3 (4.8) |
| comparative strain 3 | comparative strain 3 | 40 (6.8) | $1.6 \times 10^2$ (6.8) | $3.0 \times 10^3$ (6.8) | $7.0 \times 10^4$ (6.8) | $4.8 \times 10^9$ (4.8) |
| Pseudomonas aeruginosa | Pseudomonas aeruginosa | 90 (6.8) | 90 (6.8) | $1.4 \times 10^2$ (6.8) | $1.8 \times 10^2$ (6.8) | $7.2 \times 10^6$ (6.8) |
| Pseudomonas aeruginosa + | Pseudomonas aeruginosa | 90 (6.8) | 86 (6.8) | 90 (6.8) | $1.0 \times 10^2$ (6.7) | 5 (4.9) |
| comparative strain 3 | comparative strain 3 | 40 (6.8) | $1.5 \times 10^2$ (6.8) | $4.2 \times 10^3$ (6.8) | $7.6 \times 10^4$ (6.8) | $2.4 \times 10^8$ (5.4) |

Figure in parenthesis shows pH of medium.

TABLE 3-5

| | | shaking time (hr) | | | | |
|---|---|---|---|---|---|---|
| added bacteria | measured strains | 0 (theoretical number of added bacteria) | 3 | 6 | 9 | 24 |
| comparative strain 4 | comparative strain 4 | 57 (6.8) | $2.1 \times 10^2$ (6.8) | $1.5 \times 10^3$ (6.8) | $1.2 \times 10^4$ (6.8) | $9.0 \times 10^8$ (4.7) |
| Escherichia Coli | Escherichia Coli | 16 (6.8) | 14 (6.8) | $8.3 \times 10^2$ (6.8) | $2.8 \times 10^4$ (6.8) | $1.1 \times 10^9$ (5.6) |
| Escherichia Coli + | Escherichia Coli | 16 (6.8) | 18 (6.8) | $7.4 \times 10^2$ (6.8) | $8.4 \times 10^3$ (6.8) | $1.4 \times 10^6$ (5.1) |
| comparative strain 4 | comparative strain 4 | 57 (6.8) | $2.0 \times 10^2$ (6.8) | $1.3 \times 10^3$ (6.8) | $1.0 \times 10^4$ (6.8) | $6.2 \times 10^8$ (5.1) |
| Salmonella typhimurium | Salmonella typhimurium | 91 (6.8) | 29 (6.8) | $1.6 \times 10^3$ (6.8) | $6.3 \times 10^3$ (6.8) | $1.2 \times 10^9$ (5.8) |
| Salmonella typhimurium + | Salmonella typhimurium | 91 (6.8) | 8 (6.8) | $6.3 \times 10^2$ (6.8) | $2.4 \times 10^4$ (6.8) | $1.2 \times 10^8$ (4.9) |
| comparative strain 4 | comparative strain 4 | 57 (6.8) | $2.9 \times 10^2$ (6.8) | $1.2 \times 10^3$ (6.8) | $1.4 \times 10^4$ (6.8) | $8.2 \times 10^8$ (4.9) |
| Pseudomonas aeruginosa | Pseudomonas aeruginosa | 88 (6.8) | 35 (6.8) | 33 (6.8) | 44 (6.8) | $1.7 \times 10^7$ (6.9) |
| Pseudomonas aeruginosa + | Pseudomonas aeruginosa | 88 (6.8) | 21 (6.8) | 29 (6.8) | 31 (6.8) | 0 (4.7) |
| comparative strain 4 | comparative strain 4 | 57 (6.8) | $2.0 \times 10^2$ (6.8) | $2.4 \times 10^3$ (6.8) | $1.1 \times 10^4$ (6.8) | $3.4 \times 10^9$ (4.7) |

Figure in parenthesis shows pH of medium.

TABLE 3-6

| | | shaking time (hr) | | | | |
|---|---|---|---|---|---|---|
| added bacteria | measured strains | 0 (theoretical number of added bacteria) | 3 | 6 | 9 | 24 |
| comparative strain 5 | comparative strain 5 | $1.2 \times 10^3$ (6.8) | 7 (6.1) | $7.8 \times 10^3$ (6.7) | $4.1 \times 10^2$ (6.4) | $9.0 \times 10^6$ (4.6) |
| Escherichia Coli | Escherichia Coli | $3.2 \times 10^2$ (6.8) | $3.2 \times 10^2$ (6.2) | $2.7 \times 10^4$ (6.1) | $2.7 \times 10^5$ (6.7) | $4.9 \times 10^9$ (5.2) |
| Escherichia Coli + | Escherichia Coli | $3.2 \times 10^2$ (6.8) | $4.0 \times 10^2$ (6.8) | $4.2 \times 10^4$ (6.8) | $8.2 \times 10^4$ (6.8) | $3.6 \times 10^8$ (4.9) |
| comparative | comparative | $1.2 \times 10^3$ | 10 | 72 | $3.8 \times 10^4$ | $2.5 \times 10^6$ |

TABLE 3-6-continued

| added bacteria | measured strains | 0 (theoretical number of added bacteria) | shaking time (hr) | | | |
|---|---|---|---|---|---|---|
| | | | 3 | 6 | 9 | 24 |
| strain 5 | strain 5 | | (6.1) | (6.3) | (6.5) | (4.9) |
| Salmonella typhimurium | Salmonella typhimurium | $1.2 \times 10^3$ (6.8) | $5.2 \times 10^3$ (6.6) | $1.8 \times 10^5$ (6.6) | $2.8 \times 10^6$ (6.3) | $4.5 \times 10^9$ (5.2) |
| Salmonella typhimurium + comparative strain 5 | Salmonella typhimurium | $1.2 \times 10^3$ (6.8) | $4.4 \times 10^3$ (6.5) | $6.6 \times 10^4$ (6.7) | $1.4 \times 10^6$ (6.4) | $9.2 \times 10^7$ (5.0) |
| | comparative strain 5 | $1.2 \times 10^3$ (6.8) | 17 (6.5) | $3.3 \times 10^3$ (6.7) | $3.5 \times 10^4$ (6.4) | $1.9 \times 10^6$ (5.0) |
| Pseudomonas aeruginosa | Pseudomonas aeruginosa | 46 (6.8) | $1.1 \times 10^2$ (6.5) | $1.2 \times 10^2$ (6.6) | $1.3 \times 10^2$ (6.2) | $6.5 \times 10^6$ (6.6) |
| Pseudomonas aeruginosa + comparative strain 5 | Pseudomonas aeruginosa | 46 (6.8) | 93 (6.2) | $1.0 \times 10^2$ (6.5) | $1.1 \times 10^2$ (6.2) | $1.8 \times 10^3$ (4.5) |
| | comparative strain 5 | $1.2 \times 10^3$ (6.8) | 13 (6.2) | $6.9 \times 10^3$ (6.5) | $3.7 \times 10^2$ (6.2) | $1.8 \times 10^6$ (4.5) |

Figure in parenthesis shows pH of medium.

TABLE 3-7

| added bacteria | measured strains | 0 (theoretical number of added bacteria) | shaking time (hr) | | | |
|---|---|---|---|---|---|---|
| | | | 3 | 6 | 9 | 24 |
| comparative strain 6 | comparative strain 6 | $1.4 \times 10^2$ (6.7) | $2.3 \times 10^3$ (6.5) | $7.2 \times 10^3$ (6.6) | $5.6 \times 10^8$ (6.6) | $1.0 \times 10^{10}$ (4.4) |
| Escherichia Coli | Escherichia Coli | 23 (6.7) | 43 (6.5) | $2.1 \times 10^3$ (6.6) | $7.5 \times 10^4$ (6.6) | $4.5 \times 10^8$ (4.8) |
| Escherichia Coli + comparative strain 6 | Escherichia Coli | 23 (6.7) | 31 (6.5) | $2.4 \times 10^3$ (6.6) | $5.8 \times 10^4$ (6.6) | $4.0 \times 10^6$ (4.7) |
| | comparative strain 6 | $1.4 \times 10^2$ (6.7) | $2.6 \times 10^2$ (6.5) | $6.4 \times 10^3$ (6.6) | $4.9 \times 10^4$ (6.6) | $1.1 \times 10^{10}$ (4.7) |
| Salmonella typhimurium | Salmonella typhimurium | 66 (6.7) | 68 (6.7) | $4.1 \times 10^3$ (6.6) | $1.1 \times 10^5$ (6.7) | $3.4 \times 10^9$ (5.6) |
| Salmonella typhimurium + comparative strain 6 | Salmonella typhimurium | 66 (6.7) | 58 (6.5) | $1.7 \times 10^3$ (6.6) | $9.0 \times 10^4$ (6.6) | 19 (4.7) |
| | comparative strain 6 | $1.4 \times 10^2$ (6.7) | $2.3 \times 10^3$ (6.5) | $7.4 \times 10^3$ (6.6) | $7.6 \times 10^4$ (6.6) | $1.8 \times 10^{10}$ (4.7) |
| Pseudomonas aeruginosa | Pseudomonas aeruginosa | 60 (6.7) | 44 (6.5) | 64 (6.6) | 58 (6.6) | $4.6 \times 10^6$ (6.8) |
| Pseudomonas aeruginosa + comparative strain 6 | Pseudomonas aeruginosa | 60 (6.7) | 23 (6.5) | 25 (6.6) | 42 (6.6) | 0 (4.5) |
| | comparative strain 6 | $1.4 \times 10^2$ (6.8) | $1.9 \times 10^2$ (6.5) | $8.0 \times 10^3$ (6.6) | $7.2 \times 10^4$ (6.6) | $4.5 \times 10^9$ (4.5) |

Figure in parenthesis shows pH of medium.

CONSIDERATION OF THE TEST RESULT

It is confirmed as shown in Table 1 that the *Lactobacillus johnsonni* F-133 according to the present invention has a higher resistance against stomach acid as compared with the lactic acid bacteria of any one of the comparative strains.

It is also confirmed as shown in Table 2 that the *Lactobacillus johnsonni* F-133 according to the present invention has an equal or higher resistance against bile acid as compared with the lactic acid bacteria of any one of the comparative strains.

It is further confirmed as shown in Tables 3-1 to 3-7 that the *Lactobacillus johnsonni* F-133 according to the present invention is remarkably effective in suppressing the growth of the above-mentioned pathogenic bacteria as compared with the lactic acid bacteria of any one of the comparative strains and therefore has a strong resistance against the pathogenic bacteria.

EXAMPLE OF APPLICATION

Description will now be made as regards the case where the strain according to the present invention is added to milk replacer fed to infant animals.

In case of a calf for example, feed is changed from mother's milk to milk replacer in an early stage in order to collect cow's milk.

Generally, intestinal floras of infant animals are greatly affected by environment and change of feed. Useful bacteria are liable to decrease while harmful bacterial such as *Escherichia coli* are liable to increase. Accordingly, diarrhea causes many infant animals' death.

Recently, antibiotics are added to milk replacer in order to avoid above-mentioned problem. In this event, there arises a new problem of unfavorable effects resulting from residual antibiotics. It is therefore necessary to find another preventive measure which can be replaced with antibiotics.

15 calfs of 5 days old are divided into three groups. The groups A, B, and C are fed by milk replacer without additives, milk replacer with lactic acid bacteria preparations according to the present invention ($10^9$/270 g of milk replacer), and milk replacer with antibiotics (including 100 ppm virginiamycin), respectively. The milk replacer is dissolved into warmed water at a concentration of 9% and fed the dissolved milk of 3 liter a day. It is found that, as compared with the group A, the groups B and C need less medical treatment and exhibit greater increase in weight. Thus, important differences are observed. It is confirmed that administration of lactic acid bacteria preparations according to the present invention is effective as well as administration of antibiotics.

FIELD OF INDUSTRIAL APPLICATION

The *Lactobacillus johnsonii* F-133 according to the present invention has a strong resistance against stomach acid and bile. Accordingly, viable cells can reach intestines through stomach. Thus, survival stability is sufficient.

The *Lactobacillus johnsonii* F-133 according to the present invention has a strong resistance against pathogenic bacteria so as to suppress the growth of pathogenic bacteria.

When lactic acid bacteria preparations using the *Lactobacillus johnsonii* F-133 are administered orally to human beings or animals, it is possible to suppress harmful bacteria in intestines and to increase useful bacteria including *Lactobacillus johnsonii* F-133.

Accordingly, lactic acid bacteria preparations using the *lactobacillus johnsonii* F-133 meet the various requirements for viable cell preparations. Excellent effects are expected in prevention and cure of diseases such as diarrhea. As a result, the preparations are useful in promotion of the growth and maintenance of the health.

We claim:

1. A biological pure culture of *Lactobacillus johnsonii* having all the identifying characteristics of FERM BP-2680.

2. A process of manufacturing a lactic acid bacteria preparation consisting essentially of the steps of: (a) inoculating *Lactobacillus johnsonii* having all the identifying characteristics of *lactobacillus johnsonii* FERM BP-2680 into a medium comprising fermentable sugar as a major carbon source; (b) cultivating said medium of step (a) under anaerobic or facultative anaerobic cultivation conditions; (c) isolating said *lactobacillus johnsonii* from said medium, and (d) drying said isolated *Lactobacillus johnsonii* with a protective agent.

3. The process according to claim 2, wherein said medium is a liquid medium containing 1 to 20% (w/v) of a sugar selected from the group consisting of glucose, fructose and sucrose; wherein said cultivating is conducted at a temperature in the range from 20° C. to 45° C. at a Ph from 3 to 8 for 10 to 24 hours.

4. The process of claim 2 wherein a bulking agent is added to control cell concentration of the *Lactobacillus johnsonni* of step (d).

5. A lactic acid bacteria preparation made by the method according to claim 2.

6. A method of suppressing harmful bacteria and increasing useful bacteria in the digestive tract of mammals, said method comprising administering to said mammals the lactic acid bacteria preparation according to claim 5.

* * * * *